United States Patent [19]

Brown et al.

[11] Patent Number: 4,601,757

[45] Date of Patent: Jul. 22, 1986

[54] NONVOLATILE PLASTICIZERS AND NAIL POLISH CONTAINING THE SAME

[75] Inventors: Wallace H. Brown, Downers Grove; Robert E. Ansel; Kevin P. Murray, both of Hoffman Estates, all of Ill.

[73] Assignee: DeSoto, Inc., Des Plaines, Ill.

[21] Appl. No.: 709,203

[22] Filed: Mar. 7, 1985

[51] Int. Cl.$^4$ .......................... C08L 1/08; C08K 5/16; C07C 101/02

[52] U.S. Cl. .................... 106/183; 106/186; 524/186; 524/199; 560/155; 560/171

[58] Field of Search ............... 106/169, 179, 178, 186, 106/183; 560/155, 171; 524/199, 186

[56] References Cited

U.S. PATENT DOCUMENTS 3,674,837 7/1972 Wirth .................................. 560/155
3,963,771 6/1976 Robson .............................. 560/155

*Primary Examiner*—Theodore Morris
*Attorney, Agent, or Firm*—Dressler, Goldsmith, Shore, Sutker & Milnamow

[57] ABSTRACT

Nonvolatile plasticizers are provided which are the carboxyl-functional amide reaction product of: (1) a secondary amine-functional adduct of an acrylate compound, like 2-hydroxyethyl acrylate or a monohydric caprolactone monoacrylate, and about one amine equivalent per acrylate group in the acrylate compound, of an organic primary amine such as a polyoxypropylene monoprimary amine having a molecular weight in the range of about 50 to about 8000; with (2) a dicarboxylic acid anhydride, like phthalic anhydride. These plasticizers have improved wetting properties and are particularly useful in nitrocellulose compositions, such as nail polish.

18 Claims, No Drawings

NONVOLATILE PLASTICIZERS AND NAIL POLISH CONTAINING THE SAME

DESCRIPTION

1. Technical Field

This invention relates to carboxylic acid amides which are useful for many purposes, and especially as nonvolatile plasticizers for solid polymers. The invention is especially directed to such plasticizers in pigmented polymeric compositions typified by nitrocellulose-based nail polish compositions.

2. Background Art

Many polymeric solids require plasticization to increase their softness and flexibility and thus enhance their utility. Indeed, a plasticizer is something which functions to increase softness and flexibility. These polymeric solids may be relatively hard, such a nitrocellulose, or they may be relatively soft, such as rubbers typified by polybutadiene elastomers. In either event, the polymeric solids are frequency pigmented. The uniform dispersion of the pigment, however, is difficult because some of the polymers do not wet the pigment well. These polymers having poor wetting properties are frequently preferred polymers, either because they are less costly or because they possess desirable properties. Poor wetting characteristics adversely influence coating utility because the substrate must be wetted to allow the coating to spread over its surface. Poor wetting also contriubtes to poor adhesion and cracking.

The plasticizers in many instances are volatile, like dioctyl phthalate. Films, coatings and molded objects in which the plastic contains a volatile plasticizer to provide the desired softness and flexibility become more rigid with time. This leads to cracking and related defects and failures, such as separation from the supporting substrate.

Nonvolatile plasticizers are available, these being illustrated by toluene sulfonamide formaldehyde resin. However, the possibility of formaldehyde release limits the acceptability of such plasticizers.

Regardless of the volatility of the plasticizers, pigment wetting is a significant problem, and it is desired to improve the capacity of the plasticized polymer composition to wet the pigment. The poor pigment wetting characteristics are usually coupled with poor substrate wetting capacity, and this is of importance for coating utility.

The problem of providing a nonvolatile plasticizer is especially difficult in nitrocellulose-based nail polish compositions. Grinding pigments into nitrocellulose involves the possibility of explosion, so it is desired to minimize the required grinding energy to reduce hazard as well as to shorten the grinding time.

Also, nitrocellulose polishes must wet the nails on which they are coated, and wetting is poor with such polishes. The nitrocellulose is too hard and must be softened for use. Nonetheless, between the brittleness of the nitrocellulose polish and the limited adhesion of the nail substrate, it is common for portions of the polish to break off. The broken-off portion is unsightly, so the residual polish must be removed and the nails recoated.

DISCLOSURE OF INVENTION

In accordance with this invention, a nonvolatile plasticizer is provided which is the carboxyl-functional amide reaction product of: (1) a secondary amine-functional adduct of an acrylate compound, such as 2-hydroxyethyl acrylate, and about one amine equivalent per acrylate group in the acrylate compound of an organic primary amine having a molecular weight in the range of about 50 to about 8000, preferably from 200 to 2000, and especially a polyoxyalkylene primary amine having the molecular weights noted; and (2) a dicarboxylic acid anhydride, such as phthalic acid anhydride.

The adduct between the amine and the acrylate is frequently referred to as a Michael adduct, and this language will sometimes be used herein.

The plasticizers of this invention may be liquid or solid at room temperature and are useful with various polymers into which they are incorporated in amounts of from about 5% to about 50%, preferably from 10% to 35%, of total resin solids. The preferred polymers are relatively hard in the absence of plasticization, and include polyvinyl chloride, polymethyl methacrylate, and copolymers containing methyl methacrylate together with monomers copolymerizable therewith and which are selected and proportioned to provide a glass transition temperature above about 20° C., preferably above 40° C., polyvinyl acetate, styrene, and copolymers containing at least 25% of vinyl acetate or styrene having a similarly high glass transition temperature, polyacrylonitrile, cellulose acetate, nitrocellulose, and the like.

Suitable copolymers which are useful in nail polish compositions are methyl methacrylate copolymers, such as a copolymer of 33% methyl methacrylate, 65% butyl methacrylate, and 2% methacrylic acid. Styrene copolymers are useful for this same purpose, such as a copolymer of 60% styrene, 28% ethyl acrylate, 10% 2-hydroxyethyl acrylate and 2% methacrylic acid.

Plasticization is not limited to relatively hard polymers. Thus, rubbers may also be plasticized in the same way, including polybutadiene elastomers. These rubbers are frequently pigmented, especially with carbon black pigments, so pigment wetting is of great importance in easing the burden of milling the pigment into the plasticized elastomer.

Referring more particularly to the components which are combined to form the carboxy amides which are the subject of this invention, the acrylate compound may contain one or more acrylate groups, and it may also contain a reactive group, such as hydroxy, carboxy, or amide group, in addition to the acrylate group or groups. It is preferred to have an hydroxy group present, as in 2-hydroxyethyl acrylate, 2-hydroxypropyl acrylate or 2-hydroxybutyl acrylate. One may also use acrylamide, or acrylic acid. Polyacrylates are also useful, such as ethylene glycol diacrylate, trimethylol propane diacrylate, pentaerythritol triacrylate, and tris-hydroxyethyl isocyanurate di- and triacrylates.

Hydroxy-functional acrylates are preferred because they are inexpensive and available, and also because they provide a carboxyl-functional amide reaction product which includes an hydroxy group to maximize wetting characteristics. However, 2-hydroxyethyl acrylate is volatile, and it is therefore preferred to use a less volatile hydroxy-functional acrylate, such as the monohydric caprolactone monoacrylate which is available from Union Carbide Corporation, Wayne, N.J., under the trade designation Tone M100.

The acrylate compound is reacted with a stoichiometric proportion of primary amine, preferably a polyoxyalkylene primary amine. The alkylene group should contain from 2-4 carbon atoms, so one may use polyoxyethylene amines and polyoxybutylene amines as well as the presently preferred polyoxypropylene amines. Hydrocarbon amines, like lauryl amine or dodecyl amine are also useful.

The amines are preferably monoprimary amines, but diprimary amines may also be used, such as polyoxyalkylene diamines. These diprimary amines are illustrated by fatty acid diamine containing 36 carbon atoms between the two primary amine groups, and by polyoxyalkylene diamine having a molecular weight of about 400. Diamines reacted with two molar proportions of monoacrylate provide spaced apart secondary amine groups which can be used for polymer growth, as by reaction with a stoichiometric deficiency of an organic diisocyanate, like isophorone diisocyanate.

The preferred amines are illustrated by a polyoxypropylene monoprimary amine having a molecular weight of about 600 which is available from Texaco, Inc. of Houston, Tex. under the trade designation Jeffamine M600. A corresponding polyoxypropylene monoprimary amine having a molecular weight of about 200 or about 4,000 would also be fully useful. By varying the molecular weight of the amine, one can vary the acid value of the carboxyl amide to provide whatever acidity is desired.

One may also employ a polyamine containing secondary amine groups in addition to the primary amine groups, such as diethylene triamine, and this is preferred when it is desired to provide a product which contains residual amine functionality or which is polymeric. When the two primary amine groups of this compound are Michael adducted with two acrylate groups, the resulting adduct contains three secondary amino hydrogen atoms to allow reaction with three anhydride groups, thus providing a tricarboxylic acid triamide when the anhydride is of the character of phthalic anhydride.

By using one primary amine group for each acrylate group, the Michael addition reaction proceeds easily at moderate temperature, typically 60° C.-70° C., to eliminate all the acrylate groups and all the primary amine groups. As is known, the Michael addition reaction strongly prefers the primary amino hydrogen atoms, so by the time the secondary amino hydrogen atoms are the only ones which remain, there are no acrylate groups left with which to react. The result is a secondary amine-functional Michael adduct.

Of course, the stoichiometry need not be exact. A slight excess of acrylate groups will provide some Michael adduct which does not contain secondary amino hydrogen atoms, but most of the product will include such atoms for subsequent reaction. A slight excess of primary amine will provide some unreacted primary amine which will later react with two molecules of dicarboxylic acid anhydride. In either event, the unwanted product is tolerated with the desired product.

The Michael adduct thus contains a single secondary amino hydrogen atom for each acrylate group which experienced a single Michael adduction reaction, and it is desired to consume all or most of this secondary amine functionality by amide formation with a polycarboxylic acid anhydride.

The amide formation reaction is itself simple and conventional since it is known that secondary amino hydrogen atoms will react with the dicarboxylic acid anhydride group to provide a carboxyl-functional amide. Indeed, this reaction is preferential to the corresponding ester-forming reaction between the dicarboxylic acid anhydride group and the hydroxy group which is optionally present herein.

One may use dicarboxylic acid anhydrides, like phthalic anhydride, succinic anhydride and adipic anhydride, and this is now preferred. Even unsaturated anhydrides, like maleic acid, may be used. This provides an unsaturated carboxyl-functional amide which can be copolymerized with alpha, beta ethylenically unsaturated monomers, such as styrene.

One may also use a tricarboxylic acid monoanhydride which contains a carboxyl group in addition to the dicarboxylic acid anhydride group, such as trimellitic anhydride. In this instance, amide formation provides two carboxyl groups for each amide group which is formed.

Polyanhydrides are also useful, such as tetracarboxylic acid dianhydrides, like benzene tetracarboxylic acid dianhydride, and thus link two of the secondary amine Michael adducts together while forming two carboxylic acid groups.

Even polymeric polyanhydrides are useful, such as a low molecular weight copolymer of styrene and maleic anhydride, which may illustratively contain from 1 to 5 moles of styrene per mole of maleic anhydride.

It is preferred to use a stoichiometric proportion of dicarboxylic acid anhydride to consume all the secondary amine groups present, but this is not essential since a small proportion of residual amine functionality is not harmful to the properties of the composition. One can also increase the reaction temperature to consume the residual amine functionality by reaction with carboxyl functionality. It is preferred to avoid excess unreacted anhydride functionality, so preferred proportions are from 0.75 to 1.0 anhydride equivalents per secondary amine equivalent. Less desirably, one can use from 0.5 to 1.5 anhydride equivalents per secondary amine equivalent. Excess anhydride groups are permissible when the Michael adduct contains hydroxy groups which can consume these excess anhydride groups by esterification. The corresponding dicarboxylic acids cannot effectively replace the anhydrides which are needed herein because use of the dicarboxylic acids leads to the presence of unreacted dicarboxylic acid or to the excessive production of polyamides which lack carboxyl functionality.

As will now be evident, there are several opportunities to form oligomers or plural branched structures in which the molecular weight of the carboxyl-functional amide reaction products of this invention can become excessive from the standpoint of plasticizer utility, but such utility is only one aspect of this invention. It is preferred to have the molecular weight range from about 350 to about 10,000, more preferably from 400 to 4000.

It will also be appreciated that the molecular weights of the reactive materials which have been referred to herein are usually calculated from the measured reactivities, and are seldom measured directly.

The selection of pigments is subject to wide variation. Iron oxide pigments, such as a synthetic brown iron oxide pigment, black iron oxide No. 7053, chrome oxide No. 7109, ultramarine blue No. 108, ultramarine rose, ultramarine violet, Mango violet, phthalocyanine blue, and the like will illustrate other pigments which may be present alone or in combination with the titanium dioxide which is presently preferred. While any type of titanium dioxide is useful, cosmetic utility prefers the anatase form which is available in commerce where it is referred to as of cosmetic grade.

The invention is illustrated in the Examples which follow, it being understood that throughout this application and in the claims which follow, all proportions are by weight, unless otherwise specified.

EXAMPLE 1

To a suitable reaction vessel, charge one mole (344 gms) of hydroxy-functional caprolactone monoacrylate (Union Carbide product Tone M100 may be used) and one mole (581 gms) of polyoxypropylene monoprimary amine having a molecular weight of about 600 (Jeffamine M600 from Texaco Inc., Houston, Tex. may be used). The mixture is heated to 60° C. to 70° C. and held in this temperature range for about 1.5 hours to complete the Michael addition of the amine to the acrylate double bond, thus forming a secondary amine. One mole (148 gms) of phthalic anhydride is added slowly to prevent the temperature from exceeding 80° C. as the anhydride is added and the amide-forming reaction occurs. The product is a liquid carboxy-functional amide.

EXAMPLE 2

Example 1 is repeated using one mole (423 gms) of tris hydroxyethyl isocyanurate triacrylate, three moles (1743 gms) of Jeffamine M600 and three moles of phthalic anhydride.

EXAMPLE 3

The products of Examples 1 and 2 are mixed into ¼ sec. RS nitrocellulose and dissolve easily at the proportions indicated in the Table which follows. In each instance, a dried coating containing the nitrocellulose is tested to determine its knoop hardness as reported in the Table in which the percentages are based on the total weight of resin solids.

TABLE

|  | 0% | 10% | 20% | 30% | 45% |
| --- | --- | --- | --- | --- | --- |
| Example 1 | 12.8 | 12.5 | 11.4 | 9.0 | 7.7 |
| Example 2 | 12.8 | 12.8 | 12.2 | 9.0 | 7.5 |

As can be seen, the Example 1 product was more effective when used in smaller amounts, but both were effective to soften the nitrocellulose.

EXAMPLE 4

The compositions tested in Example 3, and others with different amounts of the plasticizers of Examples 1 and 2, are pigmented with titanium dioxide, anatase, by incorporating the pigment in various amounts and grinding to a Hegman N.S. rating of about 7.0. The inclusion of the Example 1 and 2 carboxyl-functional amide plasticizers eased the grinding burden, and the better grindability was noticeable when the proportion of plasticizer was as low as 5% to 10% of the weight of the pigment. These pigmented compositions can be modified by the addition of colored pigments to provide desired coloration, and are then useful as nail polishes.

EXAMPLE 5

Example 1 is repeated using one mole of a polyoxypropylene diamine having a molecular weight of about 400, two moles of Tone M100 and two moles of phthalic anhydride. Corresponding results are obtained.

EXAMPLE 6

Example 5 is repeated using one mole of fatty acid diamine in place of the polyoxypropylene diamine. Corresponding results are obtained.

EXAMPLE 7

Example 1 is repeated using one mole of n-butyl amine in place of the monoamine used in Example 1. The product is of lower molecular weight, but it still functions as a plasticizer.

EXAMPLE 8

Example 1 is repeated using one mole of maleic anhydride in place of the phthalic anhydride. The product retains the maleic unsaturation, and can be combined with styrene and copolymerized to form solid polymers in the same fashion as is commonly done with polyester-styrene blends.

EXAMPLE 9

Example 1 is repeated using one mole of a polyoxypropylene monoprimary amine having a molecular weight of about 4,000. Corresponding results are obtained.

What is claimed is:

1. The carboxyl-functional amide reaction product of: (1) a secondary amine-functional adduct of an acrylate compound and about one amine equivalent per acrylate group in the acrylate compound of an organic primary amine having a molecular weight in the range of about 50 to about 8000; with (2) a dicarboxylic acid anhydride, and said carboxyl-functional amide reaction product having a molecular weight in the range of from about 350 to about 10,000.

2. The carboxyl-functional amide reaction product recited in claim 1 in which said primary amine is an aliphatic amine having a molecular weight of from 200 to 2000.

3. The carboxyl-functional amide reaction product recited in claim 1 in which said primary amine is a polyoxyalkylene primary amine containing from 2–4 carbon atoms in the alkylene group.

4. The carboxyl-functional amide reaction product recited in claim 1 in which said dicarboxylic acid anhydride is phthalic anhydride.

5. The carboxyl-functional amide reaction product recited in claim 1 in which said dicarboxylic acid anhydride is maleic anhydride.

6. The carboxyl-functional amide reaction product recited in claim 1 in which said acrylate compound contains a reactive group selected from hydroxy, carboxy, or amide, groups.

7. The carboxyl-functional amide reaction product recited in claim 1 in which said acrylate compound is selected from 2-hydroxyethyl acrylate, 2-hydroxypropyl acrylate and 2-hydroxybutyl acrylate.

8. The carboxyl-functional amide reaction product recited in claim 1 in which said acrylate compound is a monohydric caprolactone monoacrylate.

9. The carboxyl-functional amide reaction product recited in claim 1 in which said carboxyl-functional amide reaction product has a molecular weight in the range of from 400 to 4000.

10. A plasticizer constituted by the carboxyl-functional amide reaction product recited in claim 1.

11. A solid polymer plasticized with from about 5% to about 50% of total resin solids of the carboxyl-functional amide reaction product of claim 1.

12. A solid polymer as recited in claim 11 in which said composition is pigmented.

13. A solid polymer as recited in claim 12 in which said solid polymer is relatively hard.

14. A solid polymer as recited in claim 13 in which said solid polymer has a glass transition temperature above about 40° C.

15. A solid polymer as recited in claim 13 in which said pigment is titanium dioxide.

16. A solid polymer as recited in claim 13 in which said carboxyl-functional amide reaction product is present in an amount of from 10% to 35%.

17. A relatively rigid plastic as in claim 13 in which said plastic is selected from polyvinyl chloride, polymethyl methacrylate, polyvinyl acetate, polystyrene, copolymers of the aforesaid having a glass transition temperature above 20° C., cellulose acetate and nitrocellulose.

18. A nail polish composition comprising nitrocellulose containing from about 5% to about 50% of total resin solids of the carboxyl-functional amide reaction product of claim 10.

* * * * *